(12) United States Patent
Detre et al.

(10) Patent No.: US 12,741,048 B2
(45) Date of Patent: Sep. 22, 2026

(54) PHOTOCATALYTIC AIR TREATMENT

(71) Applicant: Dyson Technology Limited, Wiltshire (GB)

(72) Inventors: Mark Kristof Detre, Bristol (GB); Kenneth Mark Armstrong, Bristol (GB)

(73) Assignee: Dyson Technology Limited, Malmesbury (GB)

( * ) Notice: Subject to any disclaimer, the term of this patent is extended or adjusted under 35 U.S.C. 154(b) by 943 days.

(21) Appl. No.: 18/008,256

(22) PCT Filed: Apr. 22, 2021

(86) PCT No.: PCT/GB2021/050966
§ 371 (c)(1),
(2) Date: Dec. 5, 2022

(87) PCT Pub. No.: WO2021/255411
PCT Pub. Date: Dec. 23, 2021

(65) Prior Publication Data

US 2023/0201411 A1 Jun. 29, 2023

(30) Foreign Application Priority Data

Jun. 16, 2020 (GB) ..................................... 2009158

(51) Int. Cl.
*A61L 9/20* (2006.01)

(52) U.S. Cl.
CPC .................................. *A61L 9/205* (2013.01)

(58) Field of Classification Search
CPC . A61L 9/205; A61L 2/08; A61L 2/232; B01D 53/007; B01D 53/885;

(Continued)

(56) References Cited

U.S. PATENT DOCUMENTS 5,790,934 A 8/1998 Say et al.
5,919,422 A 7/1999 Yamanaka et al.
(Continued)

FOREIGN PATENT DOCUMENTS

CN 101091924 A 12/2007
CN 101199922 A 6/2008
(Continued)

OTHER PUBLICATIONS

Search Report received for GB Application No. 2009158.3, mailed on Dec. 7, 2020, 1 page.

(Continued)

*Primary Examiner* — Xiuyu Tai
(74) *Attorney, Agent, or Firm* — Tucker Ellis LLP; Michael G. Craig

(57) ABSTRACT

There is provided a photocatalytic reactor including reaction chamber arranged to receive an airflow including one or more airborne contaminants. The reaction chamber includes a first inner surface, a second inner surface, a photo-catalyst for photocatalytic degradation of one or more of the contaminants disposed upon both the first inner surface and the second inner surface, and a light source arranged to illuminate at least a portion of the photo-catalyst disposed on the first inner surface and the second inner surface. The first inner surface and the second inner surface have distinct parabolic arc-shaped profiles and the profile of the first inner surface is a mirror image of the profile of the second inner surface. The first inner surface and the second inner surface may be consecutive.

13 Claims, 9 Drawing Sheets

(58) Field of Classification Search
CPC ........ B01D 2259/804; B01D 2257/708; B01D 2255/802; B01D 53/88; B01D 2257/91; B01D 2258/06; B01D 2259/4508; B01J 19/123; B01J 2219/0892; B01J 2219/32296; B01J 2219/0873; C02F 9/00; C02F 1/72; C02F 2201/3227; C02F 1/302; C02F 1/725; C02F 1/441; C02F 1/32; C02F 1/30; Y02W 10/37
See application file for complete search history.

(56) References Cited

U.S. PATENT DOCUMENTS

| | | | |
|---|---|---|---|
| 6,238,631 B1 | 5/2001 | Ogata et al. | |
| 7,935,311 B2 | 5/2011 | Katayama | |
| 7,988,923 B2 | 8/2011 | Fink et al. | |
| 8,961,890 B2 | 2/2015 | Kim | |
| 8,974,742 B2 | 3/2015 | Pastor | |
| 9,586,460 B2 | 3/2017 | Gross et al. | |
| 9,839,901 B2 | 12/2017 | Ellis et al. | |
| 10,537,870 B2 | 1/2020 | Qi et al. | |
| 2004/0018125 A1 | 1/2004 | Yang et al. | |
| 2005/0186124 A1 | 8/2005 | Fink et al. | |
| 2006/0124442 A1 | 6/2006 | Valpey et al. | |
| 2010/0149793 A1 | 6/2010 | Lai | |
| 2012/0128539 A1* | 5/2012 | Gross | A61L 9/205 422/121 |
| 2012/0141320 A1 | 6/2012 | Tupman et al. | |
| 2015/0147240 A1 | 5/2015 | Chang et al. | |
| 2015/0375187 A1 | 12/2015 | Yates et al. | |
| 2017/0261194 A1 | 9/2017 | Smits et al. | |
| 2018/0185539 A1 | 7/2018 | Keith | |
| 2019/0001015 A1 | 1/2019 | Fiedler et al. | |
| 2020/0122078 A1 | 4/2020 | Trent et al. | |
| 2023/0201756 A1 | 6/2023 | Reilly et al. | |
| 2023/0201769 A1 | 6/2023 | Zolkiewka et al. | |

FOREIGN PATENT DOCUMENTS

| | | | |
|---|---|---|---|
| CN | 202983421 | U | 6/2013 |
| CN | 204933250 | U | 1/2016 |
| CN | 105478008 | A | 4/2016 |
| CN | 106440285 | A | 2/2017 |
| CN | 106731808 | A | 5/2017 |
| CN | 206315679 | U | 7/2017 |
| CN | 107261836 | A | 10/2017 |
| CN | 111186814 | A | 5/2020 |
| EP | 0978690 | A2 | 2/2000 |
| FR | 2892951 | B1 | 3/2009 |
| JP | 09-187491 | A | 7/1997 |
| JP | H11-332965 | A | 12/1999 |
| JP | 2000-135416 | A | 5/2000 |
| JP | 2001113267 | A | 4/2001 |
| JP | 2001121000 | A | 5/2001 |
| JP | 2002273420 | A | 9/2002 |
| JP | 2004-351332 | A | 12/2004 |
| JP | 2005205094 | A | 8/2005 |
| JP | 2006-158994 | A | 6/2006 |
| JP | 2006263609 | A | 10/2006 |
| KR | 10-0660990 | B1 | 12/2006 |
| KR | 10-2017-0105805 | A | 9/2017 |
| KR | 10-2018-0035419 | A | 4/2018 |
| WO | 2007/138172 | A1 | 12/2007 |
| WO | 2011/070206 | A1 | 6/2011 |
| WO | 2014/075344 | A1 | 5/2014 |

OTHER PUBLICATIONS

Search Report received for GB Application No. 2009160.9, mailed on Dec. 14, 2022, 1 page.

International Search Report and Written Opinion received for PCT Patent Application No. PCT/GB2021/050965, mailed on Jul. 30, 2021, 10 pages.

International Search Report and Written Opinion received for PCT Patent Application No. PCT/GB2021/050966, mailed on Jul. 28, 2021, 10 pages.

International Search Report and Written Opinion received for PCT Patent Application No. PCT/GB2021/050968, mailed on Oct. 28, 2021, 16 pages.

Search Report received for GB Application No. 2009157.5, mailed on Nov. 24, 2020, 1 page.

* cited by examiner

PHOTOCATALYTIC AIR TREATMENT

CROSS-REFERENCE TO PRIOR APPLICATION

This application is a § 371 National Stage Application of PCT International Application No. PCT/GB2021/050966 filed Apr. 22, 2021, which claims the priority of United Kingdom Application No. 2009158.3, filed Jun. 16, 2020, each of which are herein incorporated by reference in their entirety.

FIELD OF THE INVENTION

The present invention relates to a photocatalytic reactor for treating an airflow, and an air treatment device comprising a photocatalytic reactor.

BACKGROUND OF THE INVENTION

An air treatment device treats air to remove contaminants. Conventional air treatment devices solely use particulate filters that physically capture airborne particles by size exclusion, with a high-efficiency particulate air (HEPA) filter removing at least 99.97% of 0.3 μm particles. Some air treatment devices use activated carbon filters to filter volatile chemicals from the air. When used for air purification, activated carbons filter out contaminants by adsorption, and therefore only have a limited capacity, such that activated carbon filters eventually require replacement if filtering performance is to be maintained. Rather than capturing contaminants it is possible to destroy certain air pollutants using techniques such as photocatalytic oxidation (PCO). Photocatalytic oxidation can be used to oxidize harmful air pollutants into less harmful compounds, for example the oxidation of volatile organic compounds (VOCs) into carbon dioxide and water. The reaction is catalysed by a catalytic surface which is activated by the absorption of photons. Moisture and oxygen from the air provide the necessary hydrogen and oxygen atoms for the reaction to progress so no reactive chemicals are consumed other than the pollutant.

SUMMARY OF THE INVENTION

According to a first aspect of the present invention there is provided a photocatalytic reactor comprising a reaction chamber arranged to receive an airflow comprising one or more airborne contaminants. The reaction chamber comprises a first inner surface, a second inner surface, a photo-catalyst for photocatalytic degradation of one or more of the contaminants disposed upon both the first inner surface and the second inner surface, and a light source arranged to illuminate at least a portion of the photo-catalyst disposed on the first inner surface and the second inner surface. The first inner surface and the second inner surface have distinct parabolic arc-shaped profiles and the profile of the first inner surface is a mirror image of the profile of the second inner surface. The first inner surface and the second inner surface may be consecutive.

The light source may comprise a light-emitting diode. The first inner surface and the second inner surface may be arranged symmetrically around an optical axis of the light-emitting diode. The first inner surface and the second inner surface may be arranged such that at least a portion of the first inner surface is illuminated by a first half of the light-emitting diode and at least a portion of the second inner surface is arranged to be illuminated by a second half of the light-emitting diode.

The light source may comprise a plurality of light-emitting diodes that are each arranged to illuminate at least a portion of both the first inner surface and the second inner surface, with the first inner surface and the second inner surface being arranged symmetrically around an optical axis of each of the plurality of light-emitting diodes. The plurality of light-emitting diodes may be distributed so as to each illuminate a different portion of a length of both the first inner surface and the second inner surface. The reaction chamber may be longitudinal and the plurality of light-emitting diodes longitudinally aligned.

The reaction chamber may comprise an air inlet and an air outlet and be arranged such that an airflow passing between the air inlet and the air outlet contacts the photo-catalyst.

The reaction chamber may comprise at least one layer of transparent material that separates the photo-catalyst from the light source.

The first inner surface and the second inner surface may be separated from an outermost surface of the at least one layer of transparent material by a maximum distance of no more than 10 mm, preferably no more than 7 mm, and preferably of from 1 mm to 7 mm.

The photocatalytic reactor may comprise a plurality of reaction chambers. The plurality of reaction chambers may be distributed around a common axis, with each reaction chamber being arranged such that the first inner surface and the second inner surface face inwardly with the light source disposed centrally relative to the first inner surface and the second inner surface face. The plurality of reaction chambers may be arranged consecutively. The plurality of reaction chambers may be arranged such that the arrangement has rotational symmetry around the common axis, and preferably has n-fold rotational symmetry wherein n is equal to the number of reaction chambers.

According to a second aspect of the present invention there is provided an air treatment device comprising a photocatalytic reactor according to the first aspect.

DESCRIPTION OF THE DRAWINGS

The present invention will be described by way of example only with reference to the following figures of which.

DETAILED DESCRIPTION

An example of an improved photocatalytic reactor will now be described by way of example only with reference to FIGS. 1A and 1B. The photocatalytic reactor is denoted generally by reference number 1000. The photocatalytic reactor 1000 comprises a reaction chamber 1001 arranged to receive an airflow comprising one or more airborne contaminants and a photo-catalyst 1004 for photocatalytic degradation of one or more of the contaminants, the photo-catalyst 1004 being disposed on a substrate 1003 provided by the reaction chamber 1001. The photocatalytic reactor 1000 further comprises a light emitting diode printed circuit board ("LED PCB") 1012 comprising a printed circuit board 1008 with multiple light emitting diodes 1009 mounted to a first side 1006 of the printed circuit board 1008. The photocatalytic reactor 1000 is arranged so that the substrate 1003 is illuminated by the light emitting diodes 1009 in order to facilitate photocatalytic degradation. In particular, the substrate 1003 is arranged to shade the LED PCB 1012 such that light emitted from the light emitting diodes 1009 of the LED PCB 1012 impinges upon the substrate 1003.

Figure 1A:
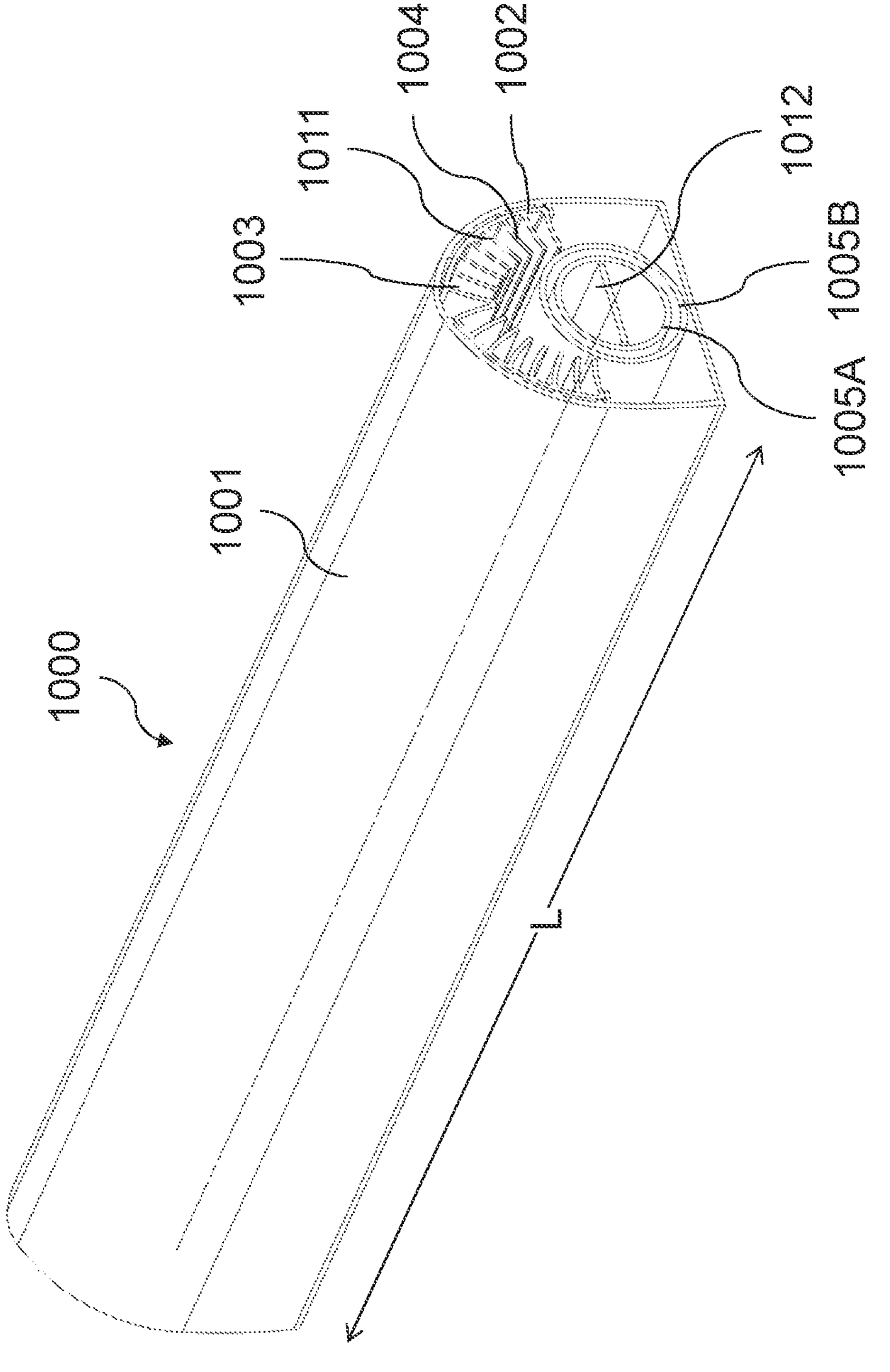
FIG. 1A is a perspective view of an example of a photocatalytic reactor for use in an air treatment device.
Figure 1B:
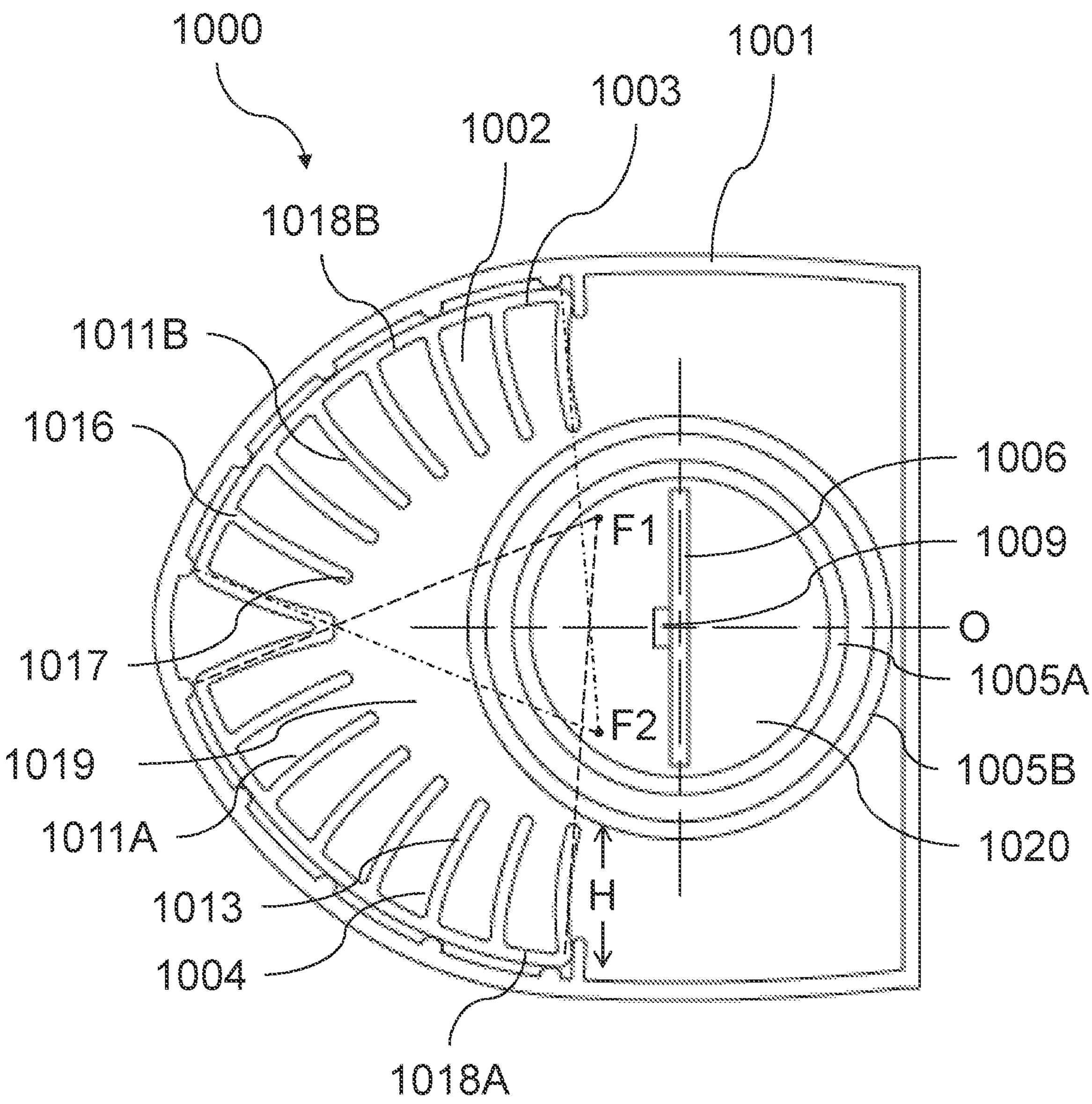
FIG. 1B is an end-on view of the photocatalytic reactor of FIG. 1A.

In the example illustrated in FIGS. 1A and 1B, the photocatalytic reactor 1000 comprises an elongate reaction chamber 1001 surrounding an elongate LED PCB 1012 that extends along the length of the reaction chamber 1001. The reaction chamber 1001 comprises a reaction chamber inlet (not shown) at a first end of the reaction chamber 1001 and a reaction chamber outlet (not shown) at a second end of the reaction chamber 1001 such that an airflow passing between the reaction chamber inlet and the reaction chamber outlet contacts the photo-catalyst 1004 disposed on the substrate 1003. A partition/barrier 1005A, 1005B then separates the photo-catalyst 1004 reaction chamber from the LED PCB 1012, with at least a portion of this partition 1005A, 1005B being transparent to the radiation emitted by the light emitting diodes 1009 so that the photo-catalyst 1004 can be illuminated by the light emitting diodes 1009. The multiple light emitting diodes 1009 of the LED PCB 1012 are then spaced apart and longitudinally aligned along the first side 1006 of the length of the LED PCB 1012, thereby providing source of light along the whole length of the photocatalytic reactor 1000.

In the example illustrated in FIGS. 1A and 1B, the substrate 1003 of the reaction chamber 1001 comprises a plurality of projections, provided by fins 1011A, 1011B, that each extend inwardly away from an inner surface of the reaction chamber 1001, with the photo-catalyst 1004 being disposed upon at least one face of each fin 1011A, 1011B. These fins 1011A, 1011B provide a high surface area for the photocatalytic degradation of contaminants. Each fin 1011A, 1011B is elongate, having a length (L) along the length of the elongate reaction chamber 1001, and a height (H) defined by how far the fin 1011A, 1011B extends inwardly away from a respective inner surface of the reaction chamber 1001. The fins 1011A, 1011B are therefore longitudinal, with a longitudinal axis of each fin 1011A, 1011B being perpendicular to an optical axis of the light-emitting diodes 1009. The fins 1011A, 1011B therefore define channels 1002 between them that extend along the length of the reaction chamber 1001 for the flow of air from the air inlet to the air outlet. In the illustrated example, each fin 1011A, 1011B has a cross-section along its height (i.e. a fin profile) that is partially curved. However, in an alternative arrangement each fin 1011A, 1011B could have a straight cross-section.

The fins 1011A, 1011B comprise a first set of fins 1011A and a second set of fins 1011B, with the photo-catalyst 1004 being disposed upon each fin. The first set of fins 1011A and the second set of fins 1011B are arranged such that light from the light emitting diodes 1009 illuminates at least a portion of the length of a face 1013 of each fin 1011A, 1011B along an entirety of the height of the face 1013. In other words, each light emitting diode 1009 illuminates the full height of at least one face 1013 of each fin 1011A, 1011B without suffering any shadowing from an adjacent fin, although multiple light emitting diodes 1009 may be required in order to illuminate the entire length of the fin 1011A, 1011B (e.g. multiple light emitting diodes distributed longitudinally). The light-emitting diodes 1009 are distributed so as to each illuminate a different, but potentially overlapping, portion of the length of at least one face 1013 of each fin 1011A, 1011B.

In the example illustrated in FIGS. 1A and 1B, each of the first set of fins 1011A is arranged such that a line extending from a base 1015 of the fin 1011A through a tip 1016 of the fin (e.g. extending along a height of the fin, similar to a chord line) is directed to a first convergence point or point of intersection (F1). Each of the second set of fins 1011B is then arranged such that a line extending from a base 1015 of the fin 1011B through the tip 1016 of the fin 1011B is directed to a second convergence point (F2). The first convergence point (F1) is different to the second convergence point (F2), and both the first convergence point (F1) and the second convergence point (F2) are offset relative to a position of the light emitting diodes 1009.

The first set of fins 1011A extend inwardly from a first inner surface 1018A of the reaction chamber 1001 and the second set of fins 1011B extend inwardly from a second inner surface 1018B of the reaction chamber 1001, with the first inner surface 1018A and the second inner surface 1018B generally facing towards the light emitting diodes 1009. The first inner surface 1018A and the second inner surface 1018B are arranged symmetrically around an optical axis (O) of the light-emitting diodes, such that the first set of fins 1011A is arranged to be illuminated by a first half of each light emitting diode 1009 and the second set of fins 1011B is arranged to be illuminated by a second half of each light emitting diode 1009. In the example illustrated in FIGS. 1A and 1B, the photo-catalyst 1004 is also disposed upon both the first inner surface 1018A and the second inner surface 1018B of the reaction chamber 1001.

The first inner surface 1018A and the second inner surface 1018B have distinct arc-shaped profiles (i.e. their cross-sections are curved segments having=different foci), with the profile of the first inner surface 1018A being a mirror image of the profile of the second inner surface 1018B. In other words, the first inner surface 1018A and the second inner surface 1018B are a reflection of one another such that together they have mirror/reflection symmetry. The first inner surface 1018A and the second inner surface 1018B may each have any of a circular arc-shaped profile and a parabolic arc-shaped profile.

In the example illustrated in FIGS. 1A and 1B, the partition 1005A, 1005B comprises two layers of transparent material disposed between and separating the light emitting diodes 1009 from the photo-catalyst 1004. These two layers of transparent material comprise a first layer of transparent material 1005A that is separated from a second layer of transparent material 1005B by a gap. These layers of transparent material 1005A, 1005B are impermeable to air and are transparent to the radiation emitted by the light emitting diodes 1009. In the example illustrated in FIGS. 1A and 1B, the two layers of transparent material 1005A, 1005B are tubular and arranged concentrically around the LED PCB 1012 with the innermost of these tubes providing a conduit within which the LED PCB 1012 is located and that is arranged to allow an airflow to pass through the conduit in order to cool the light emitting diodes 1009.

The provision of a dual-layered partition between the light emitting diodes 1009 and the photo-catalyst 1004 reduces the thermal loss between a first portion 1019 of the reaction chamber 1001 that is arranged to receive the airflow containing contaminants and a second portion 1020 containing the LED PCB 1012, thereby improving the energy efficiency. This reduction in thermal loss is particularly beneficial when implementing active cooling of the light emitting diodes 1009.

Figure 2A:
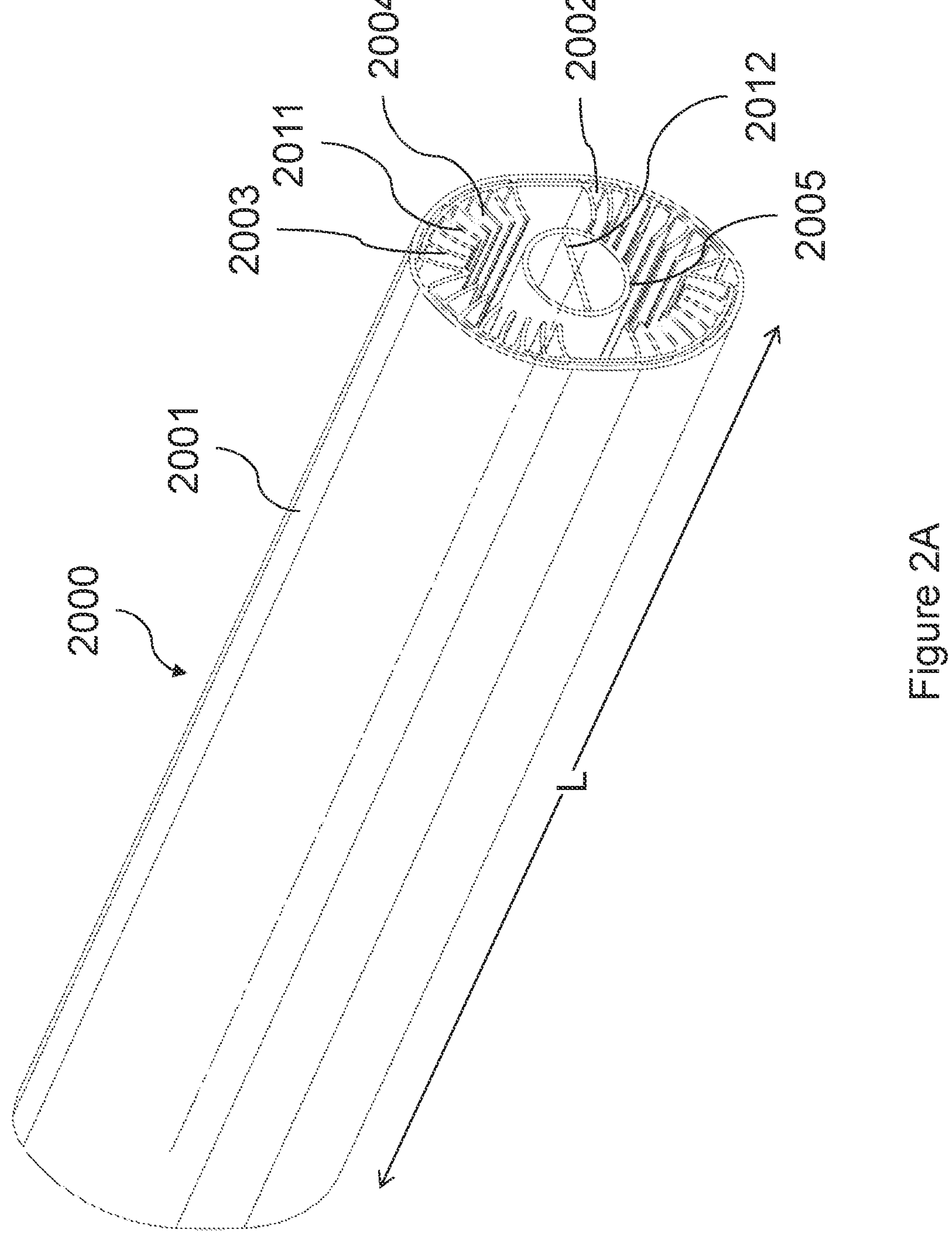
FIG. 2A is a perspective view of an example of a further photocatalytic reactor for use in an air treatment device.
Figure 2B:
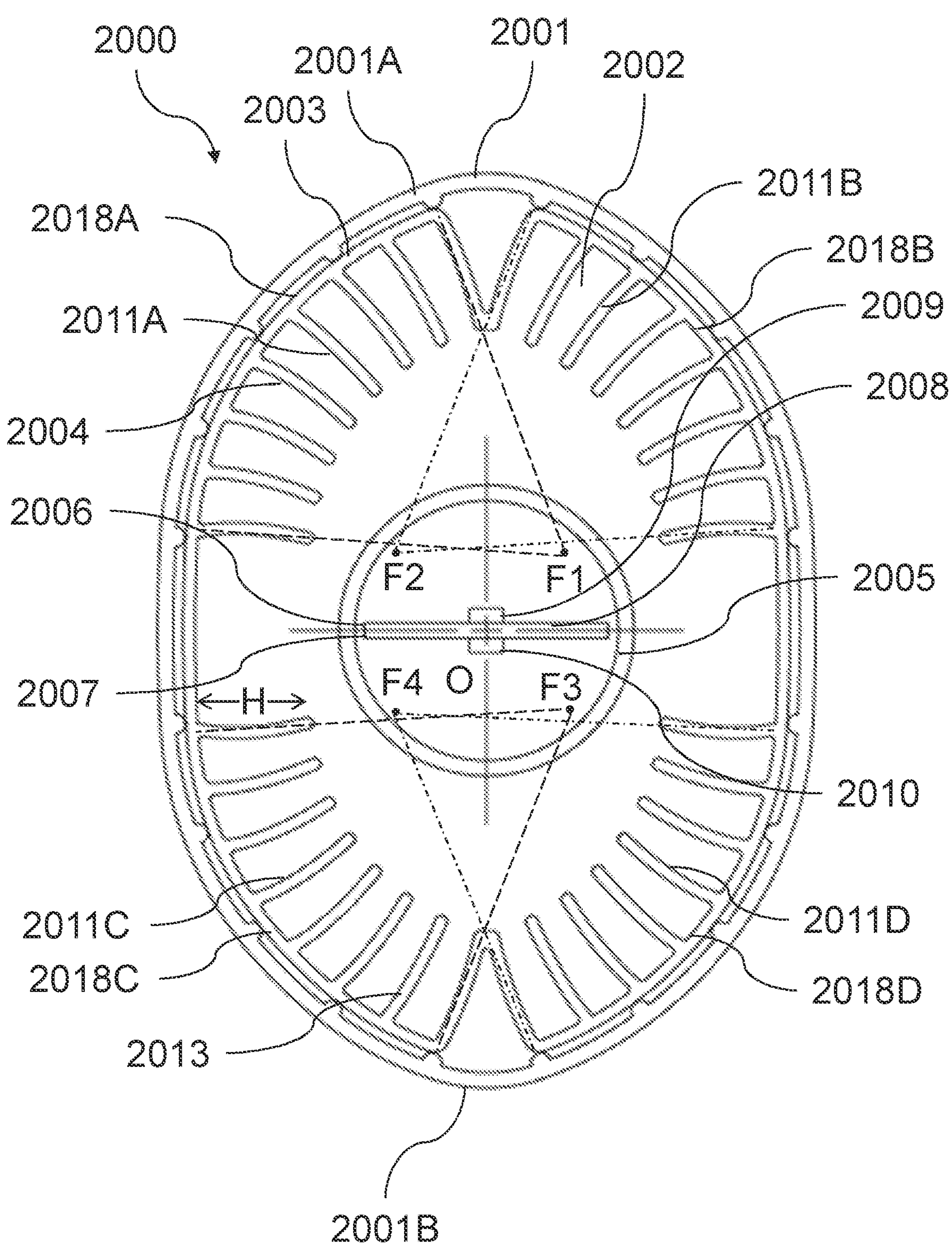
FIG. 2B is an end-on view of the photocatalytic reactor of FIG. 2A.

FIGS. 2A and 2B illustrate a further example of an improved photocatalytic reactor. The photocatalytic reactor is denoted generally by reference numeral 2000. The photocatalytic reactor 2000 comprises a reaction chamber 2001 arranged to receive an airflow comprising one or more airborne contaminants and a photo-catalyst 2004 for photocatalytic degradation of one or more of the contaminants, the photo-catalyst 2004 being disposed on a substrate 2003 provided by the reaction chamber 2001. The photocatalytic reactor 2000 is very similar to that described above with reference to FIGS. 1A and 1B, and corresponding reference numerals have therefore been used for like or corresponding parts or features of these embodiments. In particular, the photocatalytic reactor 2000 comprises an elongate reaction chamber 2001 surrounding an elongate LED PCB 2012 that extends along the length of the reaction chamber 2001. The reaction chamber 2001 comprises a reaction chamber inlet (not shown) at a first end of the reaction chamber 2001 and a reaction chamber outlet (not shown) at a second end of the reaction chamber 2001 such that an airflow passing between the reaction chamber inlet and the reaction chamber outlet contacts the photo-catalyst 2004 disposed on the substrate 2003. A partition/barrier 2005 then separates the reaction chamber 2001 from the LED PCB 2012, with at least a portion of this partition 2005 being transparent to the radiation emitted by the light emitting diodes 2009, 2010 so that the photo-catalyst 2004 can be illuminated by the light emitting diodes 2009, 2010.

In the example illustrated in FIGS. 2A and 2B, the LED PCB 2012 is dual-sided. The LED PCB 2012 therefore comprises a printed circuit board 2008 with multiple first light emitting diodes 2009 mounted to a first side 2006 of the printed circuit board and multiple second light emitting diodes 2010 mounted to a second side 2007 of the printed circuit board. The LED PCB 2012 therefore comprises any of a double-sided circuit board and a multi-layer circuit board. The first light emitting diodes 2009 of the LED PCB 2012 are spaced apart and longitudinally aligned along the first side 2006 of the length of the LED PCB 2012, and the second light emitting diodes 2010 are spaced apart and longitudinally aligned along the second side 2007 of the length of the LED PCB 2012, thereby providing a source of light along the whole length of the photocatalytic reactor 2000.

The photocatalytic reactor 2000 is then arranged so that the substrate 2003 is illuminated by both the first light emitting diodes 2009 and the second light emitting diodes 2010 in order to facilitate photocatalytic degradation. In particular, the substrate 2003 is arranged to shade the LED PCB 2012 such that light emitted from the light emitting diodes 2009, 2010 of the LED PCB 2012 impinges upon the substrate 2003. To do so, the substrate 2003 is arranged to surround the LED PCB 2012.

In the example illustrated in FIGS. 2A and 2B, the reaction chamber 2001 of the photocatalytic reactor 2000 is also dual-sided. The reaction chamber 2001 therefore comprises a first side 2001A and a second side 2001B, with the first side 2001A being arranged to be illuminated by the first light emitting diodes 2009 provided on the first side 2006 of the printed circuit board 2008 and the second side 2001B being arranged to be illuminated by the second light emitting diodes 2010 provided on the second side 2007 of the printed circuit board 2008.

The provision of a dual-sided photocatalytic reactor reduces the length of the reactor without compromising the overall volume, which is particularly important when integrating the photocatalytic reactor into a domestic air treatment device, and also reduces the material costs, especially those costs associated with the partition 2005A, 2005B and the printed circuit board 2008.

The first 2001A and second sides 2001B of the reaction chamber 2001 then individually replicate the finned arrangement of the reaction chamber 1001 illustrated in FIGS. 1A and 1B. Specifically, the first side 2001A of the reaction chamber 2001 comprises a first set of fins 2011A and a second set of fins 2011B, and the second side 2001B of the reaction chamber 2001 comprises a third set of fins 2011C and a fourth set of fins 2011D, with the photo-catalyst 2004 being disposed upon at least one face 2013 of each fin 2011. The first set of fins 2011A and the second set of fins 2001B are arranged such that light from the first light emitting diodes 2009 illuminates at least a portion of the length of a face 2013 of each fin 2011A, 2011B along an entirety of the height of the face 2013. The third set of fins 2011C and the fourth set of fins 2011D are then arranged such that light from the second light emitting diodes 2010 illuminates at least a portion of the length of a face 2013 of each fin 2011C, 2011D along an entirety of the height of the face 2013.

On the first side 2001A of the reaction chamber 2001, each of the first set of fins 2011A is arranged such that a line extending from a base 2015 of the fin 2011A through a tip 2016 of the fin (e.g. extending along a height of the fin, similar to a chord line) is directed to a first convergence point or point of intersection (F1). Each of the second set of fins 2011B is then arranged such that a line extending from a base 2015 of the fin 2011B through the tip 2016 of the fin 2011B is directed to a second convergence point (F2). The first convergence point (F1) is different to the second convergence point (F2), and both the first convergence point (F1) and the second convergence point (F2) are offset relative to a position of the first light emitting diodes 2009.

Correspondingly, on the second side 2001B of the reaction chamber 2001, each of the third set of fins 2011C is arranged such that a line extending from a base 2015 of the fin 2011C through a tip 2016 of the fin is directed to a third convergence point or point of intersection (F3). Each of the fourth set of fins 2011D is then arranged such that a line extending from a base 2015 of the fin 2011D through the tip 2016 of the fin 2011D is directed to a fourth convergence point (F4). The third convergence point (F3) is different to the fourth convergence point (F4), and both the third convergence point (F3) and the fourth convergence point (F4) are offset relative to a position of the second light emitting diodes 2010.

The first set of fins 2011A extend inwardly from a first inner surface 2018A on the first side 2001A of the reaction chamber 2001 and the second set of fins 2011B extend inwardly from a second inner surface 2018B on the first side 2001B of the reaction chamber 2001, with the first inner surface 2018A and the second inner surface 2018B generally facing towards the first light emitting diodes 2009. The third set of fins 2011C extend inwardly from a third inner surface 2018C on the second side 2001B of the reaction chamber 2001 and the fourth set of fins 2011D extend inwardly from a fourth inner surface 2018D on the second side 2001B of the reaction chamber 2001, with the third inner surface 2018C and the fourth inner surface 2018D generally facing towards the second light emitting diodes 2010.

As can be seen from FIGS. 2A and 2B, the LED PCB 2012 is located centrally within a volume of space defined by the substrate 2003. The partition 2005 then comprises a single layer of transparent material disposed between and separating the light emitting diodes 2009, 2010 from the photo-catalyst 2004. This layer of transparent material is impermeable to air and is transparent to the radiation emitted by the light emitting diodes 2009, 2010. In the example illustrated in FIGS. 2A and 2B, the single layer of transparent material 2005 is tubular and is arranged concentrically around the LED PCB 3012. This tube of transparent material 2005 provides a conduit within which the LED PCB 1012 is located and that is arranged to allow an airflow to pass through the conduit in order to cool the light emitting diodes 2009, 2010.

Those skilled in the art will realise that is it possible to combine the key features of the photocatalytic reactors of FIGS. 1A, 1B, 1A and 1B. A further example of an improved photocatalytic reactor will therefore now be described with reference to FIGS. 3A and 3B. The photocatalytic reactor is denoted generally by reference numeral 3000. The photocatalytic reactor 3000 comprises a reaction chamber 3001 arranged to receive an airflow comprising one or more airborne contaminants and a photo-catalyst 3004 for photocatalytic degradation of one or more of the contaminants, the photo-catalyst 3004 being disposed on a substrate 3003 provided by the reaction chamber 3001. The photocatalytic reactor 3000 is very similar to that described above with reference to FIGS. 2A and 2B, and corresponding reference numerals have therefore been used for like or corresponding parts or features of these embodiments. In particular, the photocatalytic reactor 3000 comprises an elongate reaction chamber 3001 surrounding an elongate LED PCB 3012 that extends along the length of the reaction chamber 3001. The reaction chamber 3001 comprises a reaction chamber inlet (not shown) at a first end of the reaction chamber 3001 and a reaction chamber outlet (not shown) at a second end of the reaction chamber 3001 such that an airflow passing between the reaction chamber inlet and the reaction chamber outlet contacts the photo-catalyst 3004 disposed on the substrate 3003. A partition/barrier 3005A, 3005B then separates the reaction chamber 3001 from the LED PCB 3012, with at least a portion of this partition 3005A, 3005B being transparent to the radiation emitted by the light emitting diodes 3009, 3010 so that the photo-catalyst 3004 can be illuminated by the light emitting diodes 3009, 3010.

Figure 3A:
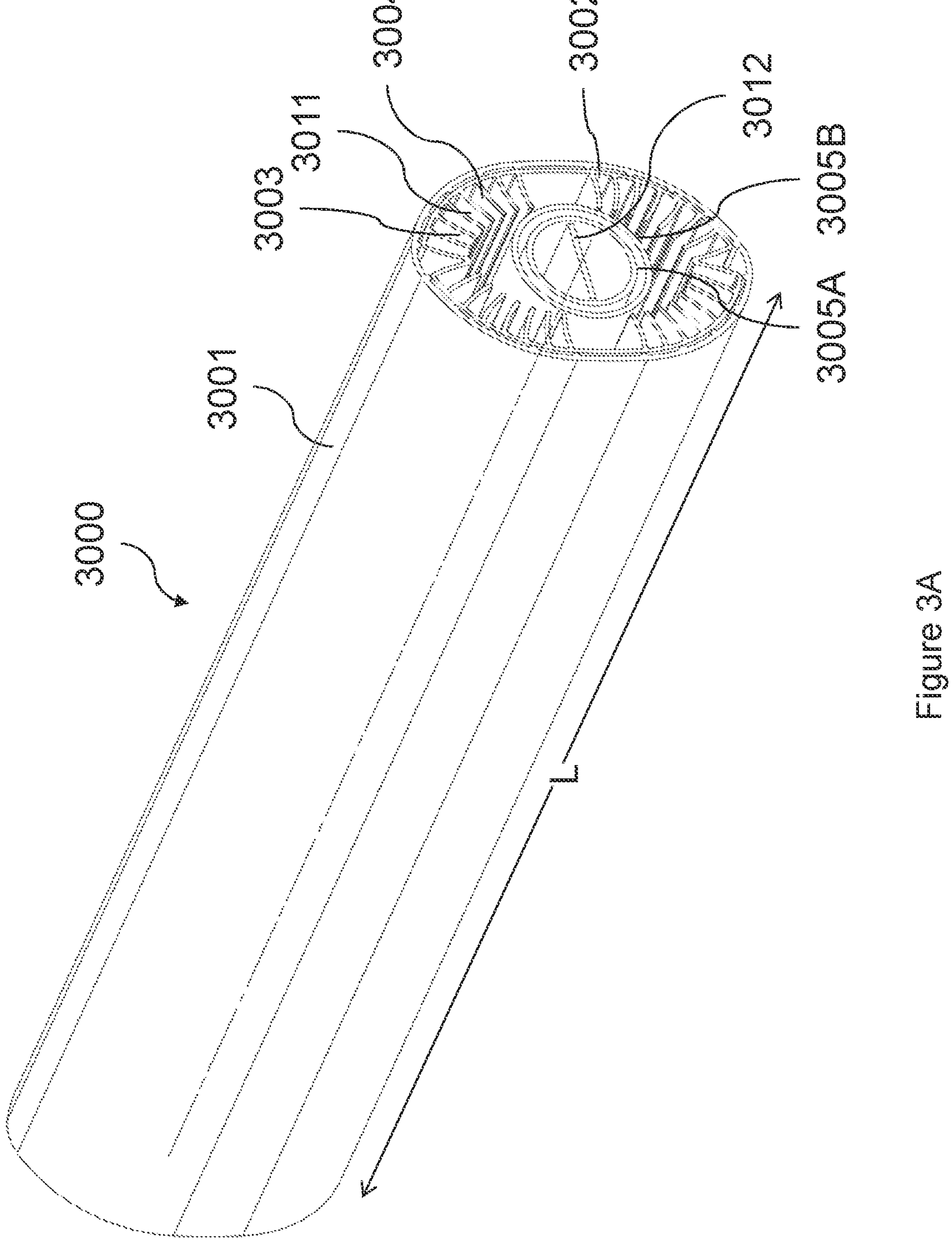
FIG. 3A is a perspective view of an example of another photocatalytic reactor for use in an air treatment device.
Figure 3B:
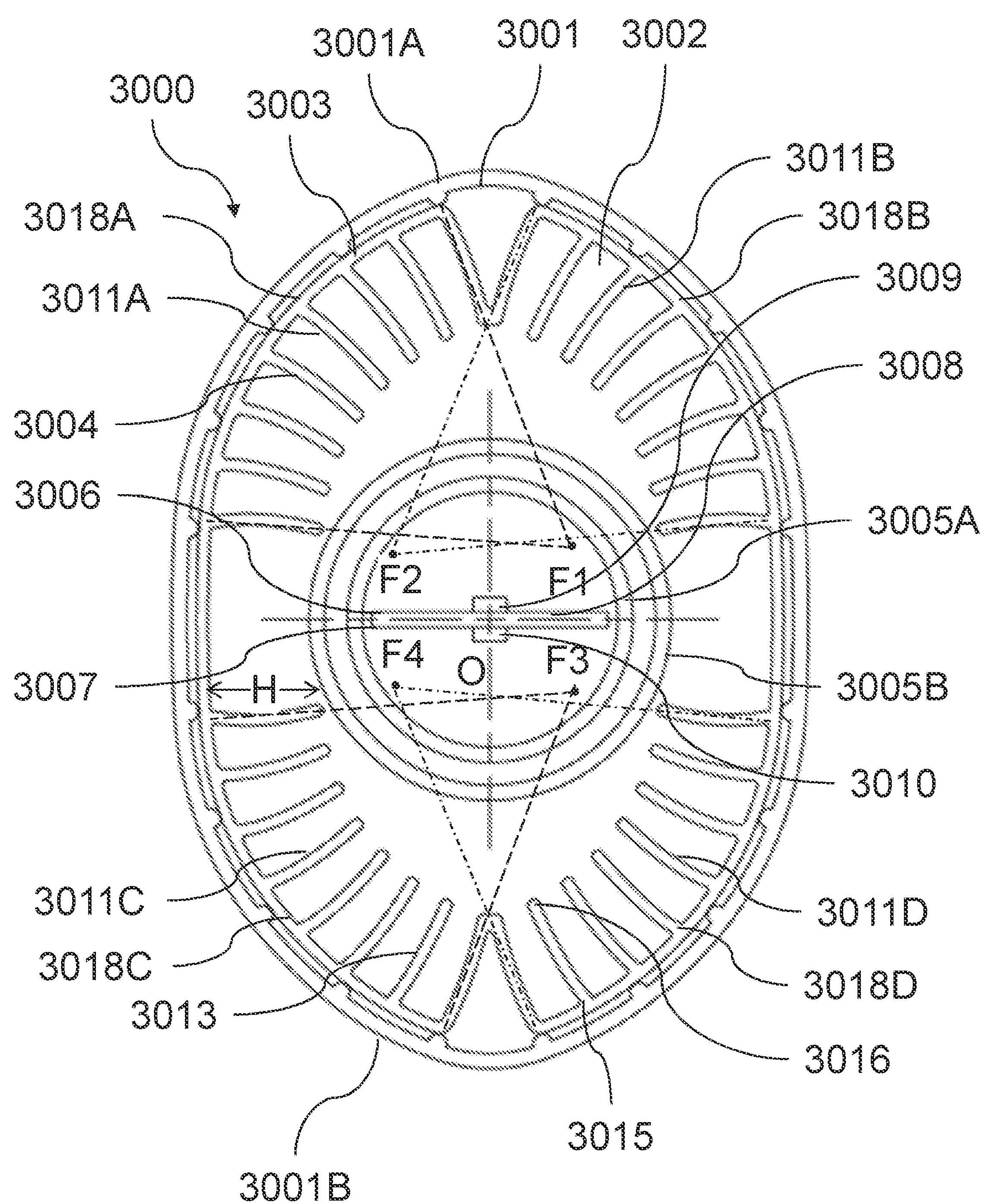
FIG. 3B is an end-on view of the photocatalytic reactor of FIG. 3A.

In the example illustrated in FIGS. 3A and 3B, both the LED PCB 3012 and the reaction chamber 3001 are dual-sided. However, unlike the example illustrated in FIGS. 2A and 2B, the partition 3005A, 3005B that separates the photo-catalyst 304 from the LED PCB 3012 comprises two layers of transparent material. These two layers of transparent material comprise a first layer of transparent material 3005A that is separated from a second layer of transparent material 3005B by a gap. These layers of transparent material 3005A, 3005B are impermeable to air and are transparent to the radiation emitted by the light emitting diodes 3009, 3010. In the example illustrated in FIGS. 3A and 3B, the two layers of transparent material 3005A, 3005B are tubular and arranged concentrically around the LED PCB 3012 with the innermost of these tubes providing a conduit within which the LED PCB 3012 is located and that is arranged to allow an airflow to pass through the conduit in order to cool the light emitting diodes 3009, 3010.

A further example of an improved photocatalytic reactor will now be described with reference to FIG. 4. The photocatalytic reactor is denoted generally by reference numeral 4000, and is shown in cross-section in FIG. 4. The photocatalytic reactor 4000 comprises three reaction chambers 4001, 4101, 4201 that are each arranged to receive an airflow comprising one or more airborne contaminants and a photo-catalyst 4004 for photocatalytic degradation of one or more of the contaminants, the photo-catalyst 4004 being disposed on a substrate 4003 provided by each of the reaction chambers 4001, 4101, 4201. The photocatalytic reactor 4000 further comprises a light emitting diode printed circuit board ("LED PCB") 4012, 4112, 4212 within each of the reaction chambers 4012, 4112, 4212. Each LED PCB 4012, 4112, 4212 comprises a printed circuit board 4008 with multiple light emitting diodes 4009 mounted to a first side of the printed circuit board 4008. The photocatalytic reactor 4000 is arranged so that the substrate 4003 provided by each of the reaction chambers 4001, 4101, 4201 is illuminated by the light emitting diodes 4009 of the corresponding LED PCB 4012, 4112, 4212 in order to facilitate photocatalytic degradation. In particular, the substrate 4003 provided by each of the reaction chambers 4012, 4112, 4212 is arranged to shade the corresponding LED PCB 4012, 4112, 4212 such that light emitted from the light emitting diodes 4009 of the LED PCB 4012, 4112, 4212 impinges upon the substrate 4003.

Figure 4:
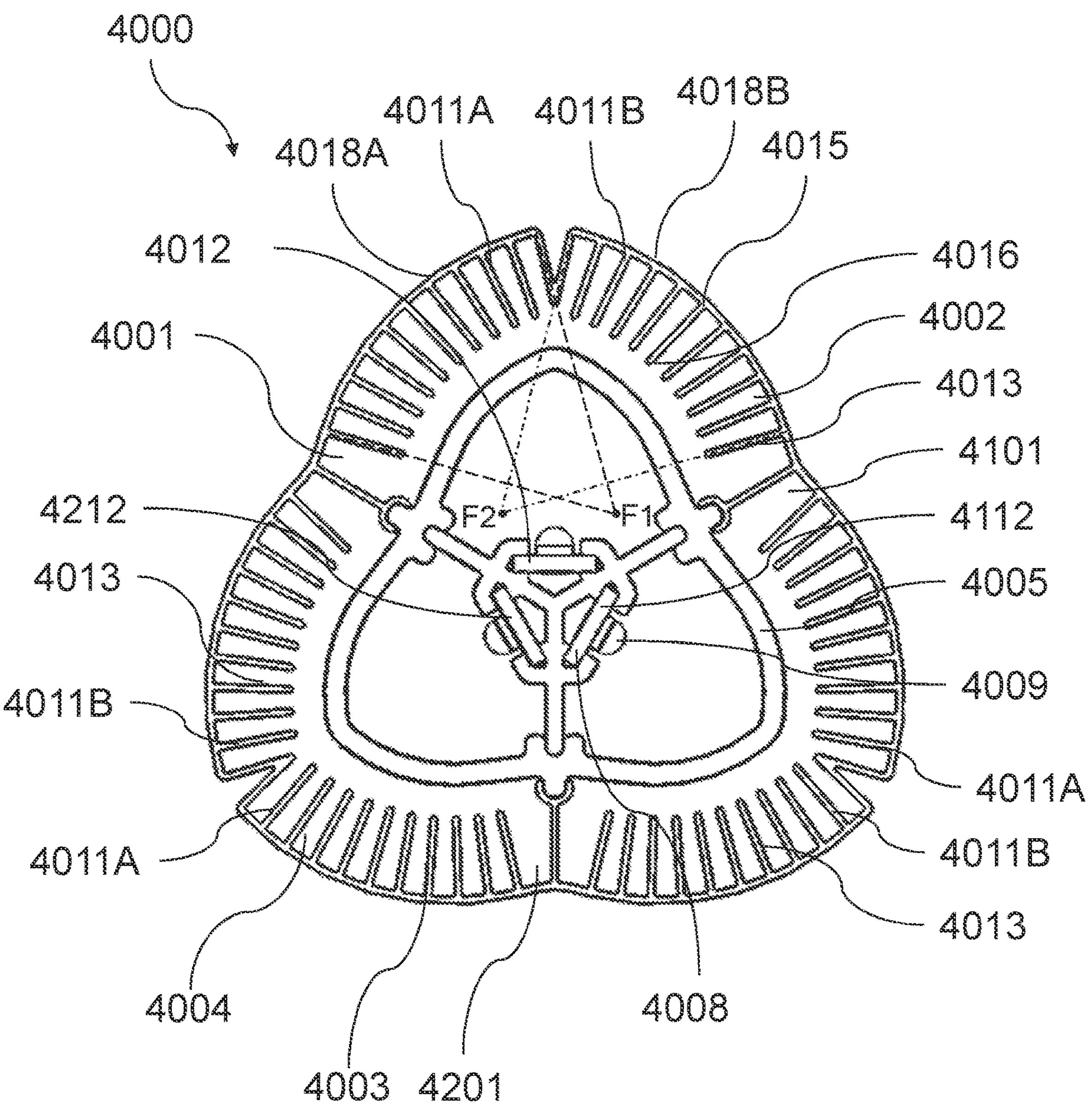
FIG. 4 is an end-on view of an example of a yet further photocatalytic reactor use in an air treatment device.

In the example illustrated in FIG. 4, each of the reaction chambers 4001, 4101, 4201 is elongate and surrounds a respective elongate LED PCB 4012, 4112, 4212 that extends along the length of the reaction chamber 4001, 4101, 4201. Each of the reaction chambers 4001, 4101, 4201 comprises a reaction chamber inlet (not shown) at a first end of the reaction chamber and a reaction chamber outlet (not shown) at a second end of the reaction chamber such that an airflow passing between the reaction chamber inlet and the reaction chamber outlet contacts the photo-catalyst 4004 disposed on the substrate 4003. A partition/barrier 4005 then separates the photo-catalyst 4004 from each LED PCB 4012, 4112, 4212, with at least a portion of this partition 4005 being transparent to the radiation emitted by the light emitting diodes 4009 so that the photo-catalyst 4004 can be illuminated by the light emitting diodes 4009. The multiple light emitting diodes 4009 of each LED PCB 4012, 4112, 4212 are then spaced apart and longitudinally aligned along the first side of the length of the printed circuit board 4008, thereby providing source of light along the whole length of the respective reaction chamber 4001, 4101, 4201.

In the example illustrated in FIG. 4, the substrate 4003 of each reaction chamber 4001, 4101, 4201 comprises a plurality of projections, provided by fins 4011A, 4011B, that each extend inwardly away from an inner surface of the reaction chamber 4001A, 4001B, 4001C, with the photo-catalyst 4004 being disposed upon at least one face of each fin 4011A, 4011B. These fins 4011A, 4011B provide a high surface area for the photocatalytic degradation of contaminants. Each fin 4011A, 4011B is elongate, having a length along the length of the elongate reaction chamber 4001A, 4001B, 4001C, and a height defined by how far the fin 4011A, 4011B extends inwardly away from a respective inner surface of the reaction chamber 4001, 4101, 4201. The fins 4011A, 4011B are therefore longitudinal, with a longitudinal axis of each fin 4011A, 4011B being perpendicular to an optical axis of the light-emitting diodes 4009. The fins 4011A, 4011B therefore define channels 4002 between them that extend along the length of the respective reaction chamber 4001, 4101, 4201 for the flow of air from the air inlet to the air outlet. In the illustrated example, each fin 4011A, 4011B has a cross-section along its height (i.e. a fin profile) that is straight. However, in an alternative arrangement each fin 4011A, 4011B could have a curved cross-section.

The fins 4011A, 4011B within each reaction chamber 4001, 4101, 4201 comprise a first set of fins 4011A and a second set of fins 4011B with the photo-catalyst 1004 being disposed upon each fin. The first set of fins 4011A and the second set of fins 4011B are arranged such that light from the corresponding light emitting diodes 4009 illuminates at least a portion of the length of a face 4013 of each fin 4011A, 4011B along an entirety of the height of the face 4013. In other words, within a reaction chamber 4001, 4101, 4201 each light emitting diode 4009 illuminates the full height of at least one face 4013 of each fin 4011A, 4011B without suffering any shadowing from an adjacent fin, although multiple light emitting diodes 4009 may be required in order to illuminate the entire length of the fin 4011A, 4011B (e.g. multiple light emitting diodes distributed longitudinally). Within each reaction chamber 4001, 4101, 4201 the light-emitting diodes 4009 are distributed so as to each illuminate a different, but potentially overlapping, portion of the length of at least one face 4013 of each fin 4011A, 4011B.

In the example illustrated in FIG. 4, within each reaction chamber 4001, 4101, 4201, each of the first set of fins 4011A is arranged such that a line extending from a base 4015 of the fin 4011A through a tip 4016 of the fin (e.g. extending along a height of the fin, similar to a chord line) is directed to a first convergence point or point of intersection (F1). Each of the second set of fins 4011B is then arranged such that a line extending from a base 4015 of the fin 4011B through the tip 4016 of the fin 4011B is directed to a second convergence point (F2). The first convergence point (F1) is different to the second convergence point (F2), and both the first convergence point (F1) and the second convergence point (F2) are offset relative to a position of the light emitting diodes 4009.

The first set of fins 4011A extend inwardly from a first inner surface 4018A of the respective reaction chamber 4001, 4101, 4201 and the second set of fins 4011B extend inwardly from a second inner surface 4018B of the respective reaction chamber 4001, 4101, 4201, with the first inner surface 4018A and the second inner surface 4018B generally facing towards the light emitting diodes 4009. The first inner surface 4018A and the second inner surface 4018B are arranged symmetrically around an optical axis of the light-emitting diodes, such that the first set of fins 4011A is arranged to be illuminated by a first half of each light emitting diode 4009 and the second set of fins 4011B is arranged to be illuminated by a second half of each light emitting diode 4009. In the example illustrated in FIG. 4, the photo-catalyst 4004 is also disposed upon both the first inner surface 4018A and the second inner surface 4018B of each reaction chamber 4001, 4101, 4201.

Within each reaction chamber 4001, 4101, 4201, the first inner surface 4018A and the second inner surface 4018B have distinct arc-shaped profiles (i.e. their cross-sections are curved segments having different foci), with the profile of the first inner surface 4018A being a mirror image of the profile of the second inner surface 4018B. In other words, the first inner surface 4018A and the second inner surface 4018B are a reflection of one another such that together they have mirror/reflection symmetry. The first inner surface 4018A and the second inner surface 4018B may each have any of a circular arc-shaped profile and a parabolic arc-shaped profile.

As can be seen from FIG. 4, the reaction chambers 4001, 4101, 4201 are distributed around a common axis. In particular, the three reaction chambers 4001, 4101, 4201 are arranged such that the arrangement has three-fold rotational symmetry around the common axis. The three reaction chambers 4001, 4101, 4201 are also arranged consecutively such that the substrates 4003 of the reaction chambers 4001, 4101, 4201 define a volume of space within which the LED PCBs 4012, 4112, 4212 are located. The partition 4005 then comprises a single layer of transparent material disposed between and separating the LED PCBs 4012, 4112, 4212 from the photo-catalyst 4004. This layer of transparent material is impermeable to air and is transparent to the radiation emitted by the light emitting diodes 4009. In the example illustrated in FIG. 4, the single layer of transparent material 4005 has the form of a lobed tube and is arranged concentrically around the LED PCBs 4012, 4112, 4212. This lobed tube of transparent material 4005 provides a conduit within which the LED PCBs 4012, 4112, 4212 are located and that is arranged to allow an airflow to pass through the conduit in order to cool the light emitting diodes 4009.

The photocatalytic reactor 4000 described above comprises three reaction chambers. Those skilled in the art will realise that the photocatalytic reactor 4000 may comprise any number of reaction chambers. The photocatalytic reactor 4000 described above is elongate. Those skilled in the art will realise that this need not be the case.

The photocatalytic reactors of FIGS. 1A, 1B, 2A, 2B, 3A, 3B and 4 all comprise fins that are arranged to maximise the irradiated surface area and thereby maximise the efficiency of the photocatalytic reactor. In doing so, this arrangement also minimises the number of light emitting diodes that are required to illuminate the fins, as the lack of shadowing optimises the surface area irradiated by each light emitting diode.

The photocatalytic reactors of FIGS. 1A, 1B, 2A, 2B, 3A, 3B and 4 all comprise fins that provide a relatively high surface area of photo-catalyst. An example of an alternative improved photocatalytic reactor that does not comprise such fins will now be described with reference to FIGS. 5A and 5B. The photocatalytic reactor is denoted generally by reference numeral 5000. The photocatalytic reactor 5000 comprises two reaction chambers 5001, 5101 that are each arranged to receive an airflow comprising one or more airborne contaminants, and a photo-catalyst 5004 for photocatalytic degradation of one or more of the contaminants, the photo-catalyst 5004 being disposed on a substrate 5003, 5103 provided by each of the reaction chambers 5001, 5101. In the example illustrated in FIGS. 5A and 5B, the photocatalytic reactor 5000 then further comprises a dual-sided light emitting diode printed circuit board ("LED PCB") 5012. The LED PCB 5012 therefore comprises a printed circuit board 5008 with multiple first light emitting diodes 5009 mounted to a first side 5006 of the printed circuit board 5008 and multiple second light emitting diodes 5010 mounted to a second side 5007 of the printed circuit board 5008. The LED PCB 5012 therefore comprises any of a double-sided circuit board and a multi-layer circuit board.

The photocatalytic reactor 5000 is then arranged so that the substrate 5003 of the first reaction chamber 5001 is illuminated by the first light emitting diodes 5009 mounted to the first side 5006 of the printed circuit board 5008, whilst the substrate 5103 of the second reaction chamber 5101 is illuminated by the second light emitting diodes 5010 mounted to the second side 5007 of the printed circuit board 5008. In particular, the substrate 5003 of the first reaction chamber 5001 is arranged to shade the LED PCB 5012 such that light emitted from the first light emitting diodes 5009 impinges upon the substrate 5003, whilst the substrate 5103 of the second reaction chamber 5101 is arranged to shade the LED PCB 5012 such that light emitted from the second light emitting diodes 5010 impinges upon the substrate 5103.

Figure 5A:
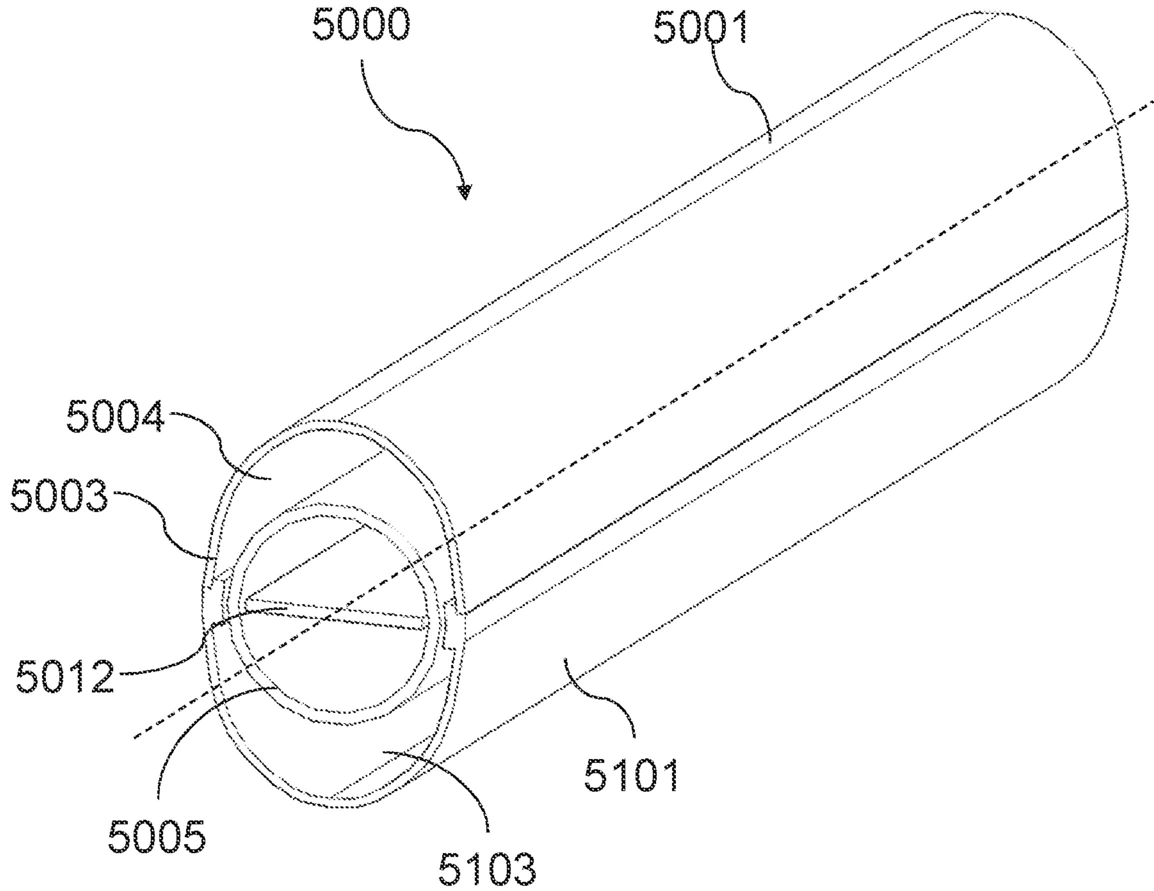
FIG. 5A is a perspective view of another example of another photocatalytic reactor for use in an air treatment device.
Figure 5B:
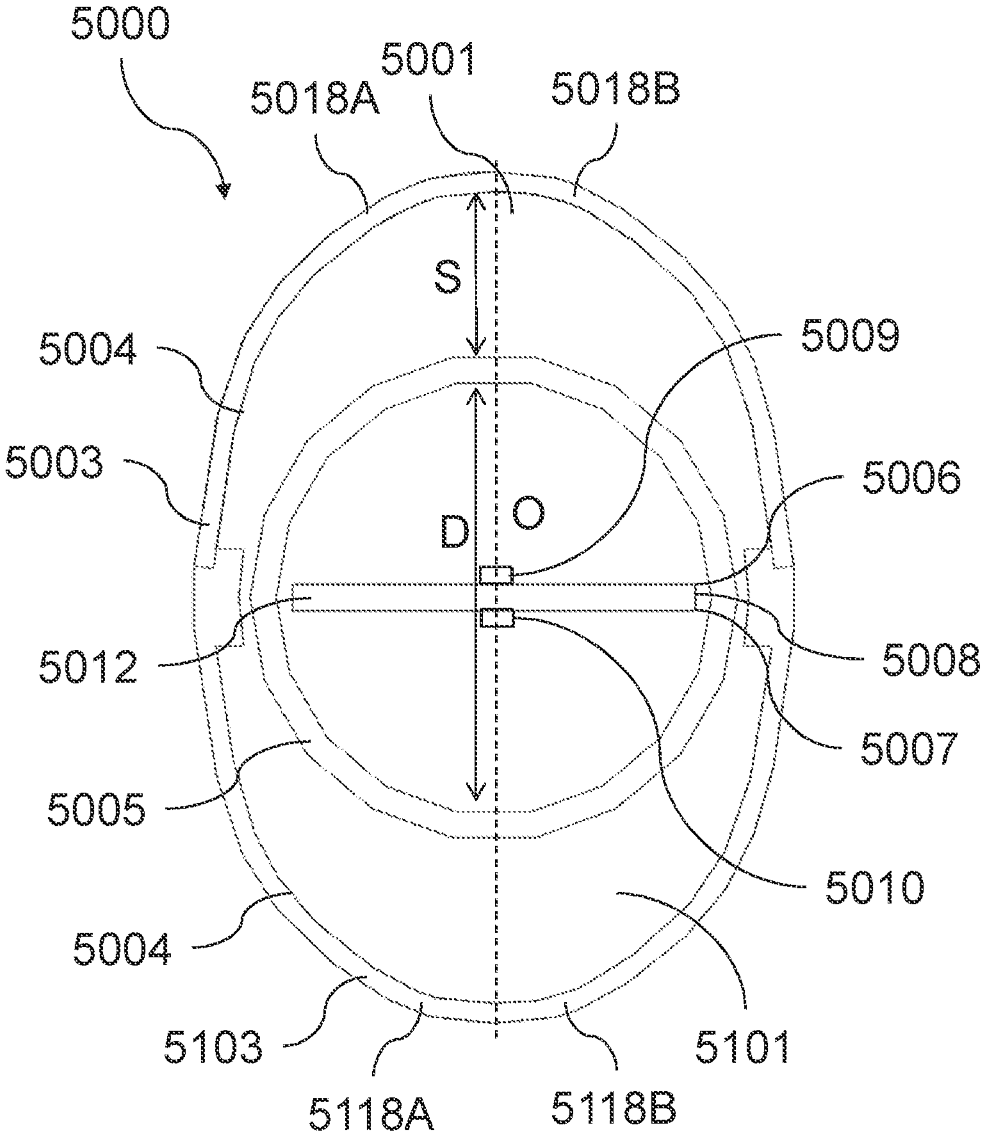
FIG. 5B is an end-on view of the photocatalytic reactor of FIG. 5A.

In the example illustrated in FIGS. 5A and 5B, the photocatalytic reactor 5000 is elongate with the first and second reaction chambers 5001, 5101 being distributed around the axis of the photocatalytic reactor 5000 such that the arrangement has two-fold rotational symmetry around the axis. The reaction chambers 5001, 5101 are also arranged consecutively such that the substrates 5003, 5103 of the reaction chambers 5001, 5101 define a volume of space within which the LED PCB 5012 is located. In particular, the LED PCB 5012 is elongate, is aligned axially within the elongate photocatalytic reactor 5000, and extends along the length of the reaction chambers 5001, 5101. The first light emitting diodes 5009 of the LED PCB 5012 are spaced apart and longitudinally aligned along the first side 5006 of the length of the LED PCB 5012, and the second light emitting diodes 5010 are spaced apart and longitudinally aligned along the second side 5007 of the length of the LED PCB 5012, thereby providing a source of light along the whole length of the photocatalytic reactor 5000.

The reaction chambers 5001, 5101 then each comprise a reaction chamber inlet (not shown) at a first end of the reaction chamber 5001, 5101 and a reaction chamber outlet (not shown) at a second end of the reaction chamber 5001, 5101 such that an airflow passing between the reaction chamber inlet and the reaction chamber outlet contacts the photo-catalyst 5004 disposed on the respective substrate 5003, 5103. A partition/barrier 5005 then separates the reaction chambers 5001, 5101 from the LED PCB 5012, with at least a portion of this partition 5005 being transparent to the radiation emitted by the light emitting diodes 5009, 5010 so that the photocatalyst 5004 can be illuminated by the light emitting diodes 5009, 5010. In the example illustrated in FIGS. 5A and 5B, the partition 5005 comprises a single layer of transparent material that is tubular and that is arranged concentrically around the LED PCB 5012. This tube of transparent material provides a conduit within which the LED PCB 5012 is located and that is arranged to allow an airflow to pass through the conduit in order to cool the light emitting diodes 5009, 5010.

In the example illustrated in FIGS. 5A and 5B, each of the reaction chambers 5001, 5101 comprises a first inner surface 5018A, 5118A and a second inner surface 5018B, 5118B, with the photo-catalyst 5004 being disposed both the first inner surface 5018A, 5118A and the second inner surface 5018B, 5118B. The first inner surface 5018A, 5118A and the second inner surface 5018B, 5118B have distinct parabolic arc-shaped profiles, meaning that their cross-sections are curved segments having different foci, with the profile of the first inner surface 5018A, 5118A being a mirror image of the profile of the second inner surface 5018B, 5118B. The photocatalytic reactor 5000 is then arranged such that the light emitting diodes 5009, 5010 of the corresponding side 5006, 5007 of the LED PCB 5012 illuminate both the first inner surface 5018A, 5118A and the second inner surface 5018B, 5118B. In particular, the first 5018A, 5118A and second inner surfaces 5018B, 5118B of each reaction chamber 5001, 5101 are arranged symmetrically around an optical axis (O) of the corresponding light-emitting diodes 5009, 5010, such that the first inner surface 5018A, 5118A is illuminated by a first half of the light-emitting diodes 5009, 5010 and the second inner surface 5018B, 5118B is arranged to be illuminated by a second half of the light-emitting diodes 5009, 5010. The first 5018A, 5118A and second inner surfaces 5018B, 5118B of each reaction chamber 5001, 5101 are also consecutive.

In the arrangement of FIGS. 5A and 5B, the lack of surface features (e.g. fins or other projections) provides that, whilst the total surface area of the photo-catalyst 5004 is reduced in comparison with the arrangements illustrated in FIGS. 1A, 1B, 2A, 2B, 3A, 3B and 4, the substrate 5003, 5103 bearing the photo-catalyst 5004 is disposed as close as possible to the light source 5009, 5010 in order to maximise the irradiance of the photo-catalyst 5004. However, a gap between the partition 5005 and the substrate 5003, 5103, is required in order to allow air to pass through the photocatalytic reactor 5000, and optimising the separation between the partition 5005 and the substrate 5003, 5103 provides for a thinner layer of air which optimises the cleaning and mixing of the air within the reaction chamber 5001, 5101. In the example illustrated in FIGS. 5A and 5B, the partition 5005 has a diameter (D) of about 35 mm, and the separation (S) between the outer surface of the partition 5005 and the substrate 5003, 5013 has a maximum of approximately 3 mm. However, the separation (S) may have a maximum of no more than 10 mm, preferably no more than 7 mm and more preferably of from 1 mm to 7 mm.

It is also desirable to produce uniform irradiance across the catalytic surface such that the air within the photocatalytic reactor is treated equally. However, LEDs do not emit light in a cylindrically-symmetrical manner but rather emit light with a Lambertian distribution. Conventional photocatalytic reactors that make use of LED light sources typically have a cylindrical substrate and therefore require a lens disposed between the LEDs and the substrate in order to evenly distribute the light emitted by the LEDs across the surface of the substrate, with the inclusion of a lens adding cost and size to the LED package. To overcome this problem, the applicant has discovered that by providing a substrate whose cross-sectional shape is defined by two distinct parabolic arcs a more uniform irradiance of the substrate may be obtained. In particular, the use of such parabolic profiles facilitates the shaping of the catalyst-bearing inner surface to take into account the local irradiance provided by the LED light sources. Such inner surfaces having parabolic profiles enables the differences in irradiance at the inner surface as a function of the angle α to be reduced, providing greater irradiance uniformity at the inner surface that is provided with photocatalyst. In this regard, the cross-sectional profile shape of each of the first 5018A, 5118A and second 5018B, 5118B inner surfaces may be defined by Bezier curves, in particular quadratic Bezier curves. The cross-sectional profile of each of the first 5018A, 5118A and second 5018B, 5118B may therefore be defined by a three points Bezier curve defined by the equation:

$$B=(1-t)^2P_0+2(1-t)tP_1+t^2P_2, t\in[0,1]$$

wherein P0 is the start point of the curve, P2 is the end point of the curve, and P1 is the control point of the curve. Using Bezier curves it is possible to provide a more uniform irradiance at the photocatalyst surface as a function of angle α.

As mentioned previously, those skilled in the art will realise that the above described photo-catalytic reactors may be used instead of a conventional photo-catalytic reactor in an air treatment device.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A photocatalytic reactor comprising:

a reaction chamber arranged to receive an airflow comprising one or more airborne contaminants, the reaction chamber comprising:

a substrate having a first inner surface, a second inner surface, a photo-catalyst for photocatalytic degradation of one or more of the contaminants disposed upon both the first inner surface and the second inner surface, and a light source arranged to illuminate at least a portion of the photo-catalyst disposed on the first inner surface and the second inner surface;

wherein the first inner surface and the second inner surface have distinct parabolic arc-shaped profiles and the profile of the first inner surface is a mirror image of the profile of the second inner surface, and wherein the first inner surface and the second inner surface are consecutive.

2. The photocatalytic reactor of claim 1, wherein the light source comprises a light-emitting diode, and the first inner surface and the second inner surface are arranged symmetrically around an optical axis of the light-emitting diode.

3. The photocatalytic reactor of claim 1, wherein the light source comprises a plurality of light-emitting diodes that are each arranged to illuminate at least a portion of both the first inner surface and the second inner surface, and the first inner surface and the second inner surface are arranged symmetrically around an optical axis of each of the plurality of light-emitting diodes.

4. The photocatalytic reactor of claim 3, wherein the plurality of light-emitting diodes are distributed so as to each illuminate a different portion of a length of both the first inner surface and the second inner surface.

5. The photocatalytic reactor of claim 3, wherein the reaction chamber is longitudinal and the plurality of light-emitting diodes are longitudinally aligned.

6. The photocatalytic reactor of claim 1, wherein the reaction chamber comprises an air inlet and an air outlet and is arranged such that an airflow passing between the air inlet and the air outlet contacts the photo-catalyst.

7. The photocatalytic reactor of claim 1, wherein the reaction chamber comprises at least one layer of transparent material that separates the photo-catalyst from the light source.

8. The photocatalytic reactor of claim 7, wherein the first inner surface and the second inner surface are separated from an outermost surface of the at least one layer of transparent material by a maximum distance of no more than 10 mm.

9. The photocatalytic reactor of claim 1, wherein the photocatalytic reactor comprises a plurality of reaction chambers.

10. The photocatalytic reactor of claim 9, wherein the plurality of reaction chambers are distributed around a common axis, with each reaction chamber being arranged such that the first inner surface and the second inner surface face inwardly and the light source is disposed centrally relative to the first inner surface and the second inner surface face.

11. The photocatalytic reactor of claim 9, wherein the plurality of photocatalytic reaction chambers are arranged consecutively.

12. The photocatalytic reactor of claim 9, wherein the plurality of reaction chambers are arranged such that the arrangement has rotational symmetry around the common axis, and preferably has n-fold rotational symmetry wherein n is equal to the number of reaction chambers.

13. An air treatment device comprising the photocatalytic reactor according to claim 1.

* * * * *